(12) United States Patent
Yamazaki et al.

(10) Patent No.: US 7,263,876 B2
(45) Date of Patent: Sep. 4, 2007

(54) APPARATUS AND METHOD OF DETECTING SURFACE CONVEXITY OF MEMBERS, AND METHOD OF PRODUCING THE MEMBERS

(75) Inventors: Junichi Yamazaki, Mishima-shi (JP); Kazuya Suzuki, Numazu-shi (JP)

(73) Assignee: Ricoh Company Limited, Tokyo (JP)

( * ) Notice: Subject to any disclaimer, the term of this patent is extended or adjusted under 35 U.S.C. 154(b) by 0 days.

(21) Appl. No.: 10/246,411

(22) Filed: Sep. 19, 2002

(65) Prior Publication Data

US 2003/0084726 A1 May 8, 2003

(30) Foreign Application Priority Data

Sep. 19, 2001 (JP) .............................. 2001-284928
Oct. 12, 2001 (JP) .............................. 2001-314849
Sep. 11, 2002 (JP) .............................. 2002-265198

(51) Int. Cl.
*G01B 5/28* (2006.01)
(52) U.S. Cl. .................................. 73/105; 73/7; 73/649
(58) Field of Classification Search ................. 73/105, 73/587, 7, 8, 649; 451/8, 10, 9
See application file for complete search history.

(56) References Cited

U.S. PATENT DOCUMENTS

| | | | | |
|---|---|---|---|---|
| 4,213,331 A | * | 7/1980 | Porter | 73/105 |
| 4,758,486 A | | 7/1988 | Yamazaki et al. | |
| 5,014,547 A | * | 5/1991 | Holroyd | 73/105 |
| 5,400,647 A | * | 3/1995 | Elings | 73/105 |
| 5,945,595 A | * | 8/1999 | Mori et al. | 73/105 |
| 6,000,282 A | * | 12/1999 | Ku et al. | 73/105 |
| 6,021,666 A | * | 2/2000 | Yao et al. | 73/105 |
| 6,296,704 B1 | | 10/2001 | Yamazaki | |
| 6,328,800 B1 | | 12/2001 | Yamazaki | |
| 2003/0015025 A1 | * | 1/2003 | Lindig | 73/105 |
| 2003/0084726 A1 | | 5/2003 | Yamazaki et al. | |

FOREIGN PATENT DOCUMENTS

| | | |
|---|---|---|
| EP | 0 599 013 | 6/1994 |
| FR | 2 671 632 | 7/1992 |
| GB | 2 074 731 | 11/1981 |
| JP | 62-189477 | 8/1987 |
| JP | 63073134 A * | 4/1988 |
| JP | 04-24773 | 2/1992 |
| JP | 05-018728 | 1/1993 |
| JP | 08005575 | 1/1996 |

(Continued)

OTHER PUBLICATIONS

U.S. Appl. No. 11/563,551, filed Nov. 27, 2006, Junichi Yamazaki et al.

*Primary Examiner*—Hezron Williams
*Assistant Examiner*—Nashmiya Fayyaz
(74) *Attorney, Agent, or Firm*—Oblon, Spivak, McClelland, Maier & Neustadt, P.C.

(57) ABSTRACT

A method of detecting a convexity present on a surface of a belt-shaped member (belt) or a roll-shaped member (roller), includes frictionizing (abrading) a surface of the member with a plate, and detecting at least one of (1) a vibration generated on the plate or (2) a change of pressure applied to the plate, to detect the convexity on the surface of the member.

14 Claims, 11 Drawing Sheets

FOREIGN PATENT DOCUMENTS

| | | |
|---|---|---|
| JP | 10010277 | 1/1998 |
| JP | 11138399 A * | 5/1999 |
| JP | 2000214100 | 8/2000 |
| JP | 2000258354 | 9/2000 |
| JP | 2000-314618 | 11/2000 |
| JP | 2001219369 A * | 8/2001 |
| WO | WO 01/44753 | 6/2001 |

* cited by examiner

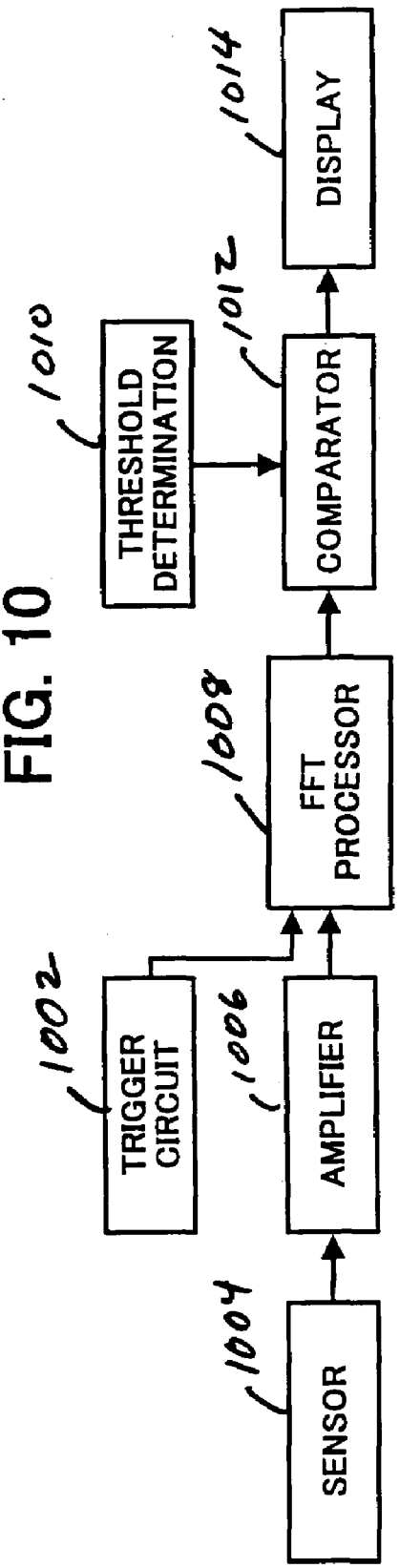
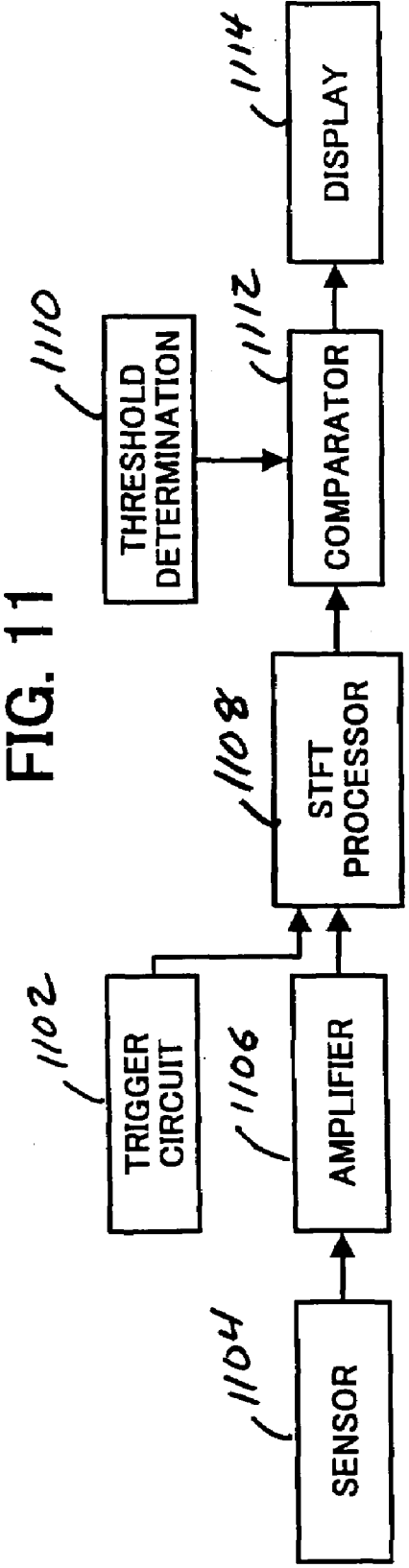

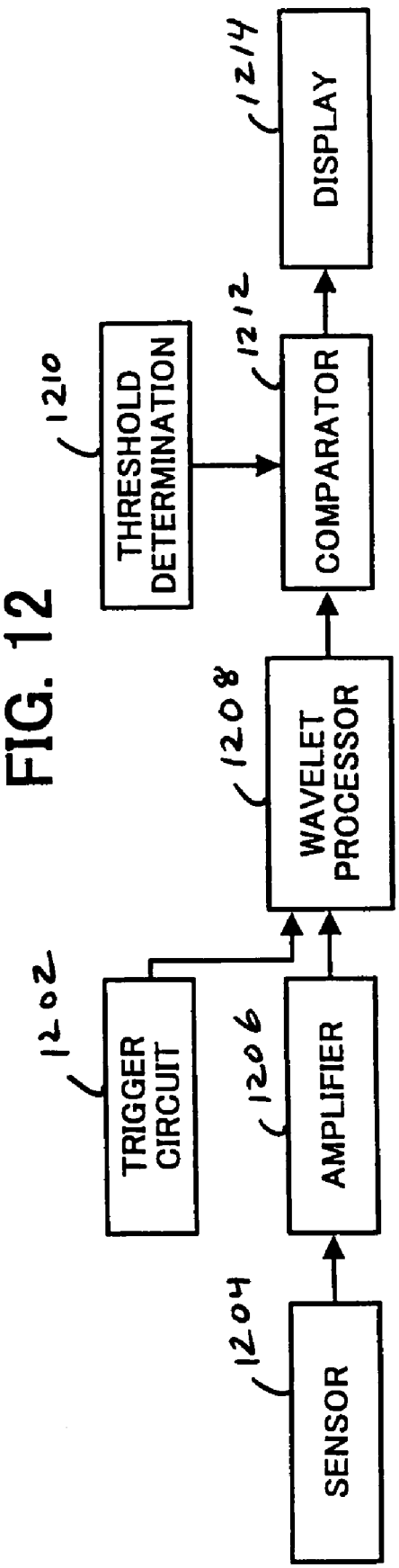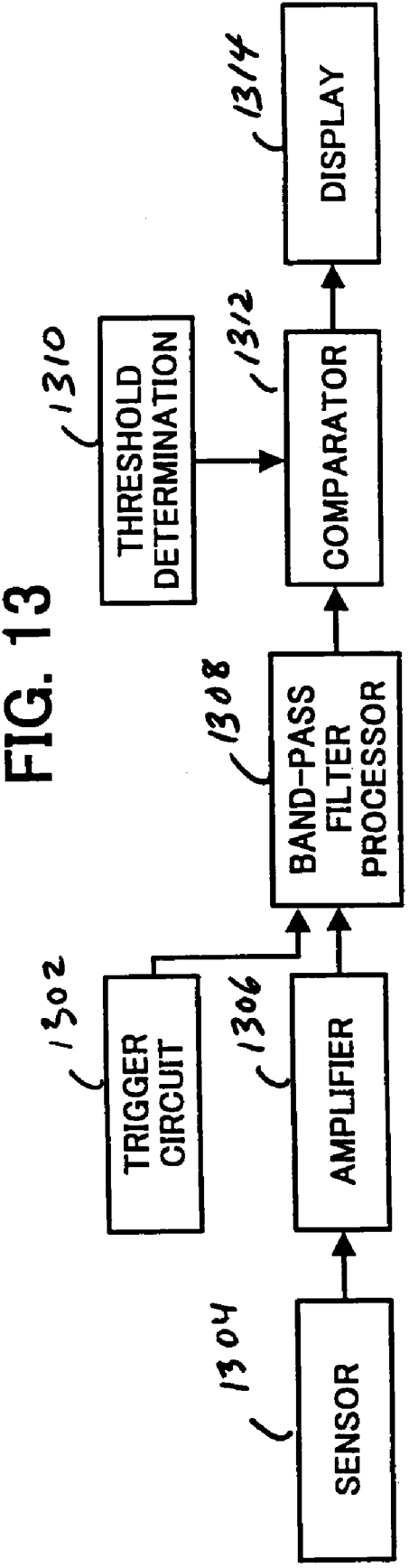

APPARATUS AND METHOD OF DETECTING SURFACE CONVEXITY OF MEMBERS, AND METHOD OF PRODUCING THE MEMBERS

BACKGROUND OF THE INVENTION

1. Field of the Invention

The present invention relates to a method and an apparatus of detecting convexity on surfaces of various belt-shaped and roll-shaped members (belts and rollers) for an electrophotographic image forming apparatus.

2. Discussion of the Background

Various types of belt-shaped and roll-shaped members (belts and rollers) are used for an electrophotographic image forming apparatus. Recently, demands for electrophotographic full-color and high-quality image forming apparatus are increasing, and members for the apparatus are required to have high quality in accordance with the demands.

The belt-shaped member (hereinafter referred to as a belt) is a flexible, seamless and cylindrical member. A metallic electroconductive substrate being a member for a photoreceptor, a photoreceptor belt bearing a latent image and including at least a photosensitive layer, and a resin made transfer belt and feeding belt mainly used for forming a full-color image are used in practice. In addition, recently, a resin-made or a metallic belt-shaped fixing belt that fixes a transferred toner image on a copy paper is being developed. Further, the above-mentioned metallic electroconductive substrate is being applied to the feeding belt or the fixing belt.

The photoreceptor belt includes at least a photosensitive layer formed on the above-mentioned metallic electroconductive substrate and a sheet photoreceptor including at least a photosensitive layer formed on an electroconductive layer of a resin film including the layer, both ends of which are bonded by an ultrasonic wave, etc.

The roll-shaped member (hereinafter referred to as a roller) is a rigid cylinder or a cylindrical member. An electroconductive metallic tube, a photoreceptor drum including a photosensitive layer formed thereon, and a charging and developing roller including a (semi) electroconductive elastic layer coated on a surface of an electroconductive metallic axis, are used in practice. An organic semiconductor, selenium and an amorphous silicone, etc., are used as a material included in the photosensitive layer of the photoreceptor drum.

These members are commonly required to have surface smoothness. Some members have a convexity or a dotted convexity impairing their smoothness, and are regarded as poor-quality members. This is because electrophotographic image forming apparatuses having such members produce poor-quality images in many cases. Therefore, the convexity has to be detected, and such members as have a convexity beyond an acceptable tolerance for an electrophotographic image forming apparatus, have to be removed in a process of producing the members.

The above-mentioned convexity will be explained, referring to examples.

The electroconductive substrate is mainly formed of nickel, stainless steel, etc. A belt substrate made of the nickel is typically produced by an electroforming method, such as an electroforming method using a nickel sulfamate liquid. When there is a foreign particle or an abnormal separation of a crystal in the liquid, the resultant nickel coated surface occasionally has a convexity.

When a photosensitive layer forming liquid is coated on the nickel belt having the convexity, there is a coating defect on the convexity, and therefore, an image forming apparatus equipped with such a photoreceptor belt produces defective images.

Coating defects are inevitable by any coating method such as a dip coating method, a spray coating method or a nozzle coating method so long as the photoreceptor belt made of nickel has such a specific convexity in greater or lesser degrees.

As a resin film for use in the above-mentioned sheet photoreceptor that is one of the photoreceptor belts, e.g., when a stretched polyethyleneterephthalate film is used, a surface waviness caused by a nonuniform stretching or bonding of both ends of the film adverse effects performance of the resultant photoreceptor.

In addition, when a belt made of a resin such as polyimide used for the transfer, feeding or fixing belt is produced by an extruder, the belt occasionally has an uneven thickness or a surface waviness. When produced by a centrifuge, the belt occasionally has a protrusion or a surface waviness. When belts having such defects are used as members of an image forming apparatus, the apparatus produces poor quality images.

Further, various convexities are formed on a surface of rollers during production, as seen in the following explanation.

When a photoreceptor drum having an organic photosensitive layer formed by a dip coating method is produced, an end of the photosensitive layer occasionally has a bubble or protrusion.

In addition, a charging or developing roller produced by coating a (semi)conductive seamless tube on a surface of a conductive metallic axis occasionally has a wrinkle in its coating or includes air or a foreign particle therein.

Various methods of detecting such convexities present on a surface of a member included in an electrophotographic image forming apparatus have been suggested, and some of them are in practical use.

For example, Japanese Laid-Open Patent Publication No. 5-18728 discloses a method of uniformly irradiating a surface of a belt with light and detecting an image while projecting a fixed pattern to detect a distortion of the pattern. However, this method has a disadvantage of requiring an optical system (such as a lens, a CCD and an image processor), and sophisticated software making a decision to pass or fail a defect.

Japanese Laid-Open Patent Publication No. 62-189477 discloses a method of producing an image by an image forming apparatus including an amorphous silicon photoreceptor and actualizing a defect of the image to detect a spherical protrusion present on the photoreceptor. However, this is a complex method because an image forming apparatus equipped with the photoreceptor has to be set up and an image has to be produced to see. In addition, a causal relation between a defect of the image and a protrusion of the photoreceptor is uncertain, and detecting accuracy is doubtful.

Japanese Laid-Open Patent Publication No. 2000-214100 discloses an apparatus pressing a first roller against a surface of a second roller in parallel, and relatively scanning a surface of the first roller to detect a protrusion based on a displacement amount of the first roller. This method has a problem that it is difficult to detect a micro protrusion because the protrusion has to move the first roller, having a mass, to be detected. In addition, this method has another problem of misidentifying a dust particle as a protrusion when the dust particle adheres to the rollers because the dust causes displacement of the first roller. Therefore, this method requires a complete dust removal and has a disadvantage of enlarging the apparatus.

Various methods are suggested to detect a protrusion even in a field other than a field of production technology of the electrophotographic image forming apparatus.

Japanese Laid-Open Patent Publication No. 2000-258354 discloses a method of irradiating light having different colors to a printed matter from different three directions. However, since it is difficult to uniformly irradiate a whole surface at a time, an inspected area becomes a small spot. Therefore, the method requires time to scan this inspection spot over the whole surface. In addition, a moderate protrusion cannot sufficiently be detected.

Japanese Laid-Open Patent Publications Nos. 8-35939 and 9-33449 disclose a method of detecting a protrusion present on a surface of a textile fabric sheet using a CCD. However, this method requires an illuminating system and a CCD, which enlarges an apparatus and does not accurately detect a moderate protrusion although it effectively detects a micro-protrusion.

Japanese Laid-Open Patent Publication No. 8-5575 discloses a method of detecting a foreign particle protrusion and a detector optically separating the foreign particle protrusion from an adhered foreign particle of a color filter, and sorting out the foreign particle protrusion that is higher than an acceptable height. However, this apparatus is complicated because it requires a transportable stage producing a XY coordinate, a color filter, and a complicated optical system. In addition, the apparatus cannot accurately detect a moderate protrusion. Further, when dust adheres to the color filter, the apparatus occasionally misidentifies the dust as a protrusion. Therefore, complete dust removal is required before inspection, and the apparatus is enlarged.

Japanese Laid-Open Patent Publication No. 10-10277 discloses a method of detecting a protrusion on an inside surface of a cylinder. However, this method has a problem of taking time to scan a gauge head over the whole inside surface of the cylinder.

As mentioned above, various convexities are frequently formed on a surface of a belt or roller that is a member of an electrophotographic image forming apparatus, which convexities are caused by its production method and directly or indirectly cause deterioration of the resultant image quality. It is desirable that the convexity be detected, and a member having a convexity beyond an acceptable tolerance be removed.

Although various methods of detecting the convexity are in practical use and suggested, they often misidentify a dust particle as a convexity and cannot accurately detect a moderate convexity or a micro-protrusion. In addition, inspection time is long, and the apparatus is complicated or large, resulting in a high cost of the inspection.

Because of these reasons, a need exists for a detection method and apparatus easily and accurately detecting a convexity present on an inside and outside surface of a belt or roller at a low cost.

SUMMARY OF THE INVENTION

Accordingly, an object of the present invention is to provide a detection method and apparatus easily and accurately detecting a convexity present on an inside and outside surface of a belt or roller at a low cost.

Another object of the present invention is to provide a detection method and apparatus easily and accurately detecting a moderate convexity or even a micro-protrusion present on an inside and outside surface of a belt or roller at a low cost.

Yet another object of the present invention is to provide a production method and a system of producing the above-mentioned belt and roller using the above-mentioned detection method and apparatus.

Briefly, these objects and other objects of the present invention as hereinafter will become more readily apparent, and can be attained by a method of detecting a convexity present on a surface of a member selected from a group including a belt-shaped member and a roll-shaped member. The method includes abrading a surface of the member with a plate, and detecting the convexity by measuring at least one of a group including vibration generated on the plate and a change of pressure applied to the contact member.

In another aspect of the present invention, a convexity detection apparatus is provided. The convexity detection apparatus is for detecting a convexity on a surface of a member selected from a group including a belt-shaped member and a roll-shaped member, and includes a plate, and a first mechanism configured to drive the member. A second mechanism causes the plate to abrade a surface of the member, and to release the plate from the member. A detector detects the convexity by measuring at least one of a group including a vibration generated on the plate and a change of pressure applied to the plate.

In yet another aspect of the present invention, a method and a system of producing a belt or a roller are provided, including at least the above-mentioned detection method and apparatus.

These and other objects, features and advantages of the present invention will become apparent upon consideration of the following description of the preferred embodiments of the present invention taken in conjunction with the accompanying drawings.

BRIEF DESCRIPTION OF THE DRAWINGS

Various other objects, features and attendant advantages of the present invention will be more fully appreciated as the same becomes better understood from the detailed description when considered in connection with the accompanying drawing (s) in which like reference characters designate like corresponding parts throughout and wherein:

FIG. 10 is a block diagram showing a mechanism performing FFT calculation;

FIG. 11 is a block diagram showing a mechanism performing a short time Fourier transform;

FIG. 12 is a block diagram showing a mechanism performing a wavelet transform;

FIG. 13 is a block diagram showing a mechanism performing a bandpass filter process;

DETAILED DESCRIPTION OF THE PREFERRED EMBODIMENTS

Figure 1:
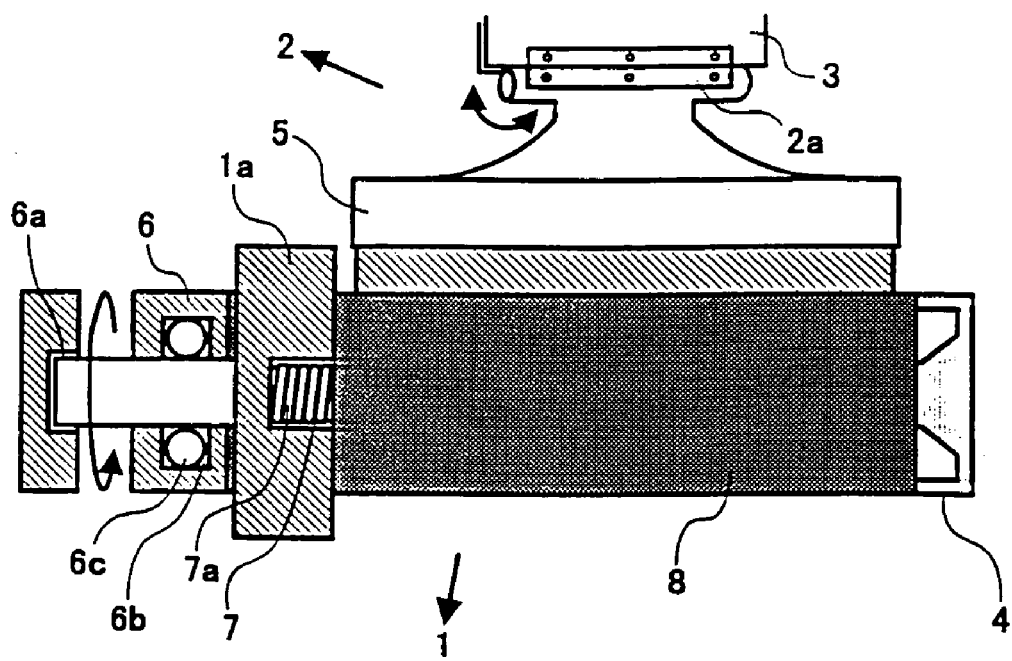
FIG. 1 is a schematic view illustrating a cross section of an application of embodiments of the detector of the present invention.

An embodiment of the present invention provides a method of detecting a convexity present on a surface of a belt or a roller, including abrading a surface of the member with a plate; and detecting a vibration generated on the plate or a change of pressure applied thereto to detect the convexity on the surface of the member.

An exemplary detector for use in the detection method of the present invention includes a plate and a mechanism for moving the plate to contact and abrade a subject (for example, belt or roller) and releasing the member therefrom. The mechanism may be located in a holder arranged at a side opposite a portion where the plate contacts the subject. A hinge connected with the holder is driven to perform abrading and release of the plate.

The belt or roller may be a member for an electrophotographic image forming apparatus, and is not particularly limited as mentioned above if the former is a flexible and seamless tube and the latter is a rigid cylinder or a cylindrical subject.

Specific examples of the belt include a metallic electroconductive substrate included in photoreceptor, a photoreceptor belt bearing a latent image and including at least a photosensitive layer and a resin-made transfer, feeding and fixing belt mainly used for forming a full-color image. Specific examples of the roller include a photoreceptor drum, a charging roller and a developing roller.

Most convexities are formed in a production process of the belt or roller. Convexity usually means a specific form, for example concavo cubic, that is part of a surface of the belt or roller and present in a body or dotted therewith. This is not the only type of convexity envisioned; other specific examples of a convexity include a protrusion, a slack, a surface waviness, a thickness irregularity, a wrinkle, a bubble, a bulge due to a mixture of air or a foreign particle, a ground swell like a moderate arc or an arcuation, or a micro-protrusion.

The convexity has a wide variety of type, number, form, size, and location, which vary depending on a member (belt or roller) or its production method.

For example, when the convexity is a protrusion, some protrusions are micro-protrusions having a diameter and a height of a few μm (micrometers) and others are large protrusions having a diameter of a few mm (millimeters) and a height of several decade μm.

As for the relative displacement of the contact portion, the belt or roller may be displaced, or the plate contacting the belt or roller may be displaced.

When the belt or roller is displaced: the belt is usually supported with a roll inside through the (cylindrical) belt and rotated by rotation of the roll; the roller itself is rotated because it is rigid.

In the present invention, the plate contacts and abrades a surface of a subject (for example, belt or roller), and when a convexity is present thereon, an end of the member vibrates and/or a pressure thereto changes due to the presence of the convexity.

Hereinafter, the portion of the plate contacting the subject (belt or roller) is referred to as a "contact portion."

The vibration or change of pressure at the contact portion has to be transmitted accurately, without decay. The composition of the plate may be varied, provided the contact portion at least detects the vibration and change of pressure. However, the contact portion preferably has a Rockwell hardness of from 65 to 140 units, and more preferably from 100 to 135 units, when measure based on JIS K 7202 (a hardness test method known to those skilled in the art). This is because the contact portion must not damage the subject, although the harder the better to accurately detect the vibration and change of pressure.

In addition, the plate preferably has a thickness of from 70 to 300 μm, and more preferably from 100 to 200 μm. The plate need not have a uniform thickness from one end to the other end (that is, a supporting portion), and the contact portion may be thinner than the supporting portion.

The contact portion typically has a width equal to or wider than a width of the subject. However, for example, when a photosensitive layer width is smaller than a photoreceptor substrate width, i.e., an effective use width of a subject is smaller than a width thereof, the effective use width can be the contact portion width.

Figure 3:
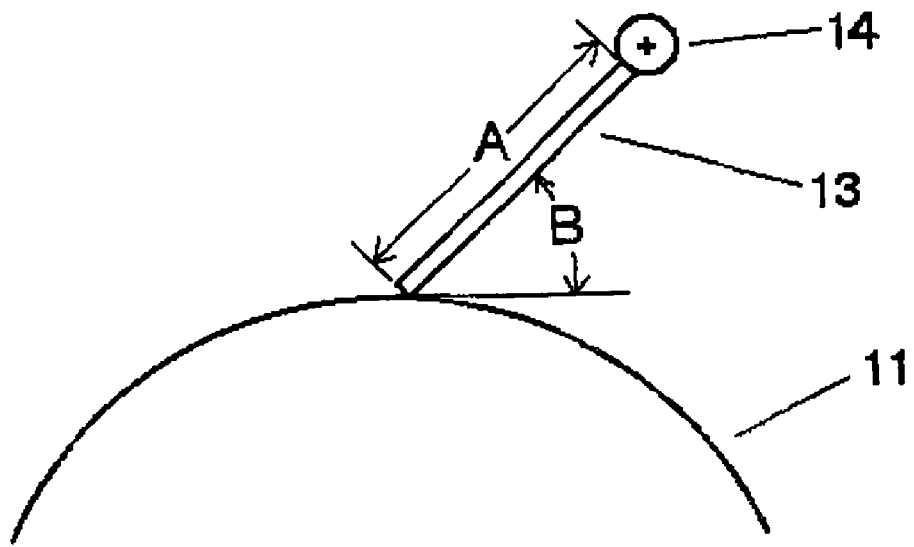
FIG. 3 is a schematic view illustrating a second embodiment of the detector of the present invention.

In addition, a length A in FIG. 3, i.e., a length between the holder of the plate and the contact portion is not shorter than 5 mm. The length is preferably from 10 to 50 mm, and more preferably from 15 to 50 mm according to a size and a detection sensitivity of an apparatus.

A material composing at least the contact portion of the plate may be varied, provided it does not damage the subject. Specific examples of the material include acrylic resins such as polyethyleneterephthalate, polybutyleneterephthalate, polyvinyl chloride, polypropylene, polystyrene, polyethylene, ultra high-molecular-weight polyethylene; plastic materials such as nylons, polycarbonate, fluorocarbon resins, polyurethane, phenol resins, urea resins, melamine-formaldehyde resins and epoxy resins; and metals such as aluminum, copper, stainless and phosphor bronze. A plastic-coated metal can also be used.

The plate may be formed of a single material and may have a different material or a thickness from that of its contact portion and holder. When the plate is formed of plural materials, the materials can be melted and adhered with a heat or can be adhered with an adhesive.

A contact angle of the plate to the subject can be optionally determined based on detection accuracy of the convexity. Namely, angle B in FIG. 3 is preferably from 30° to 80°, and more preferably from 30° to 60°.

In addition, a pressure of the plate against the subject has to be a degree so as to accurately detect the convexity but not to damage the subject. Therefore, the pressure is not limited depending on the material or size of the plate and the subject. For example, when the contact portion has a width of 40 cm, the pressure on the overall width is preferably from 0.03 to 1 N, (that is, 0.00075 to 0.025 N at a contact width of 1 cm) and more preferably from 0.05 to 0.3 N, (0.00125 to 0.025 N at a contact width of 1 cm).

The pressure distribution is preferably uniform along the overall width of the plate, and a contact side of the plate is preferably a straight line. However, according to a surface condition of the subject, the contact side may be a rectangle or a curved surface, and the contact pressure along the width direction may be changed.

The plate has to mechanically contact and be released from a surface of the subject, and various mechanical methods such as an electromagnetic solenoid, an air cylinder, a motor and a cam can be used. When the belt is held with a roll inside therethrough and rotated, the belt may be hooked on one or plural rolls, or may be hooked on and its diameter be spread by a cylindrical material capable of spreading the belt diametrically.

When the belt is hooked on the roll, the roll diameter may optionally be determined according to a size of an apparatus and is not generally limited to a particular size. However, the roll has to have such a diameter that it does not extremely bend the belt on the roll surface, and typically the diameter is preferably not less than 20 mm.

The plural rolls on which the belt is hooked are typically formed of metal, and -at least one of the rolls can have a surface layer formed of a synthetic resin or an elastic material for the purpose of improving a frictional force or cushioning effect against the seamless belt.

The roll surface layer is formed on a surface of a core material of the roll typically formed of a metal such as stainless steel and aluminum. The surface layer is optionally a semi-conductive layer in which an electroconductive material such as carbon black is included in a synthetic resin.

Specific examples of the synthetic resin include rubber-like materials such as polyurethane, a natural rubber, a butyl rubber, a nitrile rubber, a polyisoprene rubber, a polybutadiene rubber, a silicone rubber, a styrene-butadiene rubber, an ethylene-propylene rubber, an ethylene-propylene diene rubber, a chloroprene rubber, an acrylic rubber, and their mixtures. When the above-mentioned rubber materials are used, a vulcanizing agent, a vulcanizing auxiliary agent, a softener and other additives, are typically included therein. In addition, a foam material can be used as the roll surface layer. The surface layer can be formed on the above-mentioned core material by any methods such as an injection method, a press method and an extrusion method.

When the surface layer is a semi-conductive layer, a semi-conductive resin composition in which a resin-coated carbon black is included in a base resin is preferably used.

The surface layer preferably has a resistance close to that of the belt, and typically has a resistance of 10 to 1/1000 times as much as that of the belt on average. In terms of stabilizing the resistance of the belt, it is desirable that the roll surface layer has a lower resistance (higher conductivity) than that of the belt on average, and the resistance is preferably from 1/1 to 1/1000, and more preferably from 1/10 to 1/100 of the belt on average.

The relative displacement speed between the subject and the plate is preferably from 5 to 100 mm/sec, and more preferably from 20 to 50 mm/sec. At this time, the displacement speed is preferably fixed, but a change of the speed of ±30% does not largely affect detection accuracy. In addition, when the plate abrades the subject at a fixed speed and detects a vibration at a position, it is effective to make the plate abrade the position again at a different speed so as to improve detection accuracy.

The method of the present invention, using a plate as mentioned above, can particularly detect a ground swell or arcuation like a moderate arc, or a micro-protrusion.

A detection of a vibration using the plate can be made by an acoustic sense of a human as the simplest way. Namely, when the subject and the plate are manually or mechanically abraded, a convexity can be detected if a sound caused by the friction therebetween is emitted. This method is sufficiently practical.

The present invention provides a method of electrically detecting vibration that is more timesaving and efficient than the detection method of manually or mechanically abrading the subject and the plate.

As one of the methods, a peak hold processing method can be used, which method detects a vibration or a change of pressure with a vibration sensor or a pressure sensor provided with the plate, and then performs a peak hold process on the detected signal to determine a size of the peak.

As the vibration sensor and the pressure sensor for use in the present invention, various sensors can be used. For example, a piezoelectric device using a piezoelectric ceramic such as valium titanate and zirconium titanate, a condenser, a microphone, a semi-conductive pressure sensor, etc., can be used.

The typical piezoelectric device has an output voltage of from 10 to 100 mV/G and a reply frequency of from 2 to 2,000 Hz, which is sufficient for use; other piezoelectric devices can also be used if they have proper circuits.

Piezoelectric devices are classified as a unimorph type and a bimorph type, either of which can be used. When a piezoelectric device is provided, directions of vibration and the detection are preferably chosen to detect the vibration with high sensitivity.

In addition, a plate equipped with plural sensors having different frequency characteristics or different sensitivities can be used, to improve detection accuracy and expand detectable range.

For example, when a convexity present on the subject is a protrusion having a diameter of a few μm and a height of a few μm, or a diameter of a few mm and a height of several decade μm as mentioned above, both a micro-protrusion and a large ground swell can be detected if a sensor capable of detecting the micro-protrusion and a sensor capable of detecting the large ground swell are provided.

Therefore, even when protrusions or surface variations having different forms and sizes are widely spread over the subject, plural sensors can detect them while a sole sensor and a detector circuit cannot.

In addition, the plate does not have to be one plate. Plural plates can contact a surface of the subject to retain detection sensitivity. In this case, each of the plates may have a different thickness, size, material and contact pressure.

Further, a sensor equipped with the plate can be changed to effectively detect another convexity present in the width direction of the subject.

For example, even a protrusion a few μm high in an image forming area of an electrophotographic photoreceptor largely affects the resultant image quality. However, a protrusion a few μm high out of the image forming area at an end of the photoreceptor does not affect the resultant image quality at all. When an object to be detected is different according to a portion to be detected, the above-mentioned method can accurately detect a protrusion and a surface variation.

After a vibration and/or a change of pressure detected by the sensor are/is converted into an electrical signal, the peak hold process is performed on the signal to compare a maximum strength obtained from the peak hold process with a threshold.

When the peak hold process is performed, a detector is used that includes a plate equipped with at least one sensor, a mechanism performing the peak hold process on an electrical signal converted from a vibration and/or a change of pressure detected by the sensor, and a mechanism comparing a maximum strength obtained from the peak hold process with a threshold.

In order to reflect a result of the above-mentioned comparing process, an operation to be performed afterwards includes 1) removing a beyond-tolerance subject by displaying the result on a paper or a display of a displaying mechanism or 2) running a computer programmed to automatically remove or lighting a lamp to manually remove the beyond-tolerance subject, etc.

However, operational steps are not limited to the foregoing. Also, places where the comparing process and the operation afterwards are performed, need not be close to each other, and may be remote from each other. In addition, the peak hold process can be performed with an electric circuit or with software.

When a vibration sensor or pressure sensor is used, it is effective to determine its frequency distribution so as to improve detection accuracy because a signal obtained from the sensor includes signals having various frequencies. Various methods can be used to determine the frequency distribution, such as an electric circuit or software to perform a Fourier transform.

Further, the invention provides a method of improving detection sensitivity and accuracy, in which multiple resolution analysis is used to analyze a sporadic (non-continuous) signal derived from vibration of the contact portion of the plate.

In the present invention, an electrical signal from the vibration or pressure sensor provided with the plate, is digitized with an A/D converter, and the resultant digital signal is processed with multiple resolution analysis to identify a vibration or a change of pressure.

The multiple resolution analysis is a method of analyzing a time shift of a variation while analyzing a spectrum in its frequency domain. In the present invention, a short-time Fourier transform, a wavelet transform, a method of determining a Wigner(-Viret) distribution, and a method of using a bandpass filter, for example, may be used.

Therefore, a detector using a process with the multiple resolution analysis includes a plate equipped with at least one sensor, a mechanism performing the multiple resolution analysis process on an electrical signal converted from a vibration and/or a change of pressure detected by the sensor, and a mechanism comparing a result of the process with a threshold.

An operation to be performed afterwards to reflect the result of the multiple resolution analysis process is the same as that of the above-mentioned comparing process of the peak hold process method.

Four methods of the multiple resolution analysis are generally known, as mentioned in, e.g., "Wavelet Analysis" issued in June, 1997, by Kyoritsu Shuppan and written by Ryuuichi Ashino and Shizuo Yamamoto.

Since a result of the multiple resolution analysis differs and has an advantage according to each method, it is preferable in the present invention to select a method in compliance with an convexity expected based on the particular subject (belt or roller) under study.

For example, when convexities are uniform in size, the short-time Fourier transform and the Wigner(-Viret) distribution are suitable; when the convexities vary in size, the wavelet transform is suitable.

In addition, the bandpass filter method has an advantage of processing an analog signal at high speed because it can analyze both a digital signal and an analog signal.

In the present invention, a result obtained from each of the short-time Fourier transform, wavelet transform, Wigner distribution process, and bandpass filter process, is compared with results of a normal subject and an abnormal subject to make a decision to pass or fail.

In a particular example, an electret microphone from Sony Corp. is used as a microphone, and an analog signal obtained by the microphone is converted into a digital signal with an A/D converter from Burr-Brown, which signal is downloaded in a personal computer from IBM Corp. A sampling speed of the A/D conversion is 44,100 Hz and a limit of resolution is 10 bits. A process of obtaining a measured signal, the multiple resolution analysis thereof, computing the Wigner distribution, etc., are performed by software written in the C programming language.

Next, another method of improving the accuracy of the detection method of the present invention will be explained.

The method is that, in a case where the relative friction between the plate and a subject is performed by, e.g., rotation of the subject, when a convexity is detected in a rotating direction (a forward direction), the rotating direction is reversed (a reverse direction) to perform detection again at a position or a vicinity thereof where the convexity was detected in the forward direction.

This detecting operation by abrading in the forward and reverse direction can be performed even when the plate does not have a sensor. However, the plate preferably has a sensor to automatically and more precisely detect a convexity.

To further improve detection accuracy, the number of times of abrading in the forward and reverse directions is not limited to one time, and plural repetitions thereof can optionally be performed, e.g., two times thereof in the forward direction and one time thereof in the reverse direction may be performed. In addition, the speed during abrading may be changed. Moreover, a combination of the change of the number of abrading steps and a change of the speed during abrading may be used.

When a detecting operation is performed by abrading in both the forward and reverse directions, information of a detected convexity occasionally differs. By comparing the information, more precise or intimate information of the convexity, such as the size, form, number or location thereof, can be obtained. In this case, a control mechanism switching the forward and reverse directions effectively performs the operation.

In addition, when a sound or a signal detected by abrading in the forward direction is too small to identify a presence or a position of a convexity, abrading in the reverse direction can detect the convexity.

Further, abrading in the forward direction detects a presence of a convexity first, and repeated abrading in the forward and reverse directions, while optionally changing the speed of abrading, to precisely and intimately detect the convexity can improve detection accuracy.

This method can further be used to identify whether a convexity detected by abrading in the forward direction is in fact due to dust (particularly a small dust particle) adhering to a subject. When dust is identified, it can be expected that abrading in the reverse direction or repeating abrading in the forward and reverse directions of the plate, removes the dust.

Hereinafter, the detection apparatus of the present invention will be explained, referring to the drawings.

FIG. 1 is a schematic view illustrating a cross section of an application of embodiments of the detector of the present invention.

In FIG. 1, a convexity, like a protrusion on a surface of a subject that is a belt-shaped seamless metallic substrate 8 for an electrophotographic photoreceptor, is detected. The apparatus includes a member (holder 1) detachably holding the metallic substrate 8 inside thereof, a plate 5, and a plate holder 2 holding the plate. Plate holder 2 includes a hinged portion 2a that is connected to an element 3 that may be, for example, a hydraulic cylinder.

Substrate 8 is held on roll shaped holder 1. Plate 5 is driven by plate holder 2 to contact substrate 8. Then, substrate 8 is abraded while being rotated, and a contact portion of plate 5 vibrates or emits an abnormal noise at the same time due to a convexity such as a protrusion when the convexity is present on a surface of substrate 8. Thus, a convexity is detected by an operator.

In the detecting apparatus in FIG. 1, the substrate holder 1 has a wheel 6 with a shaft hole having a spline (not shown) that is connected to a rotating shaft of the substrate holder 1 with a key inserted into the spline. An end of the rotating shaft is supported by a roller bearing 6a and the other end thereof is supported by a U-type roller bearing (not shown). In FIG. 1, 6c is a bearing arranged in a space 6b.

As the rotating means, a motor can also be used instead of wheel 6.

Figure 2:
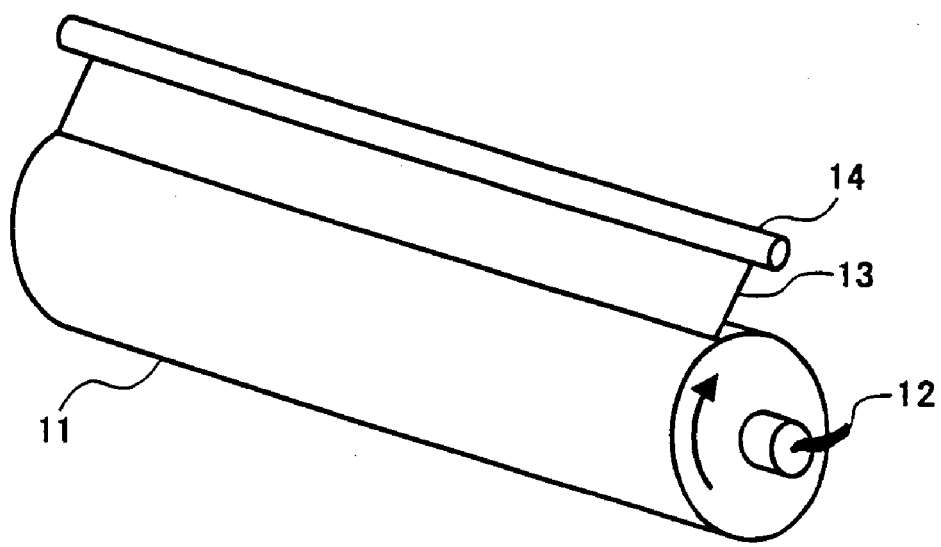
FIG. 2 is a schematic view illustrating a first embodiment of the detector of the present invention.

FIG. 2 is a schematic view illustrating a first embodiment of the detector of the present invention.

In FIG. 2, numeral 11 is a roller, or a belt supported with a roll inside, and numeral 12 is an axis therefor and rotatable in a direction indicated by an arrow. Numeral 13 is a plate and 14 is a hinge holding the plate, moving the plate into contact with a subject and releasing the plate therefrom. The plate 13 may be a polyester film having a thickness of 100 µm, a width of 25 mm and a length of 450 mm.

In FIG. 2, the plate 13 contacts and abrades a surface of the member 11 for an electrophotographic image forming apparatus, and a presence of a convexity can easily be detected when the plate 13 contacts the convexity on the surface of the member 11 and emits a vibration sound.

FIG. 3 is a schematic view illustrating a second embodiment of the detector of the present invention.

In FIG. 3, numeral 11 is a member for an electrophotographic image forming apparatus, 13 is a plate, 14 is a rotatable hinge holding the plate, A is a width of the plate, and B is an angle at which the plate contacts the member 11.

Angle B may be adjusted according to a convexity on the surface of the subject and a sensitivity of a sensor. Depending on a form of the subject and a contact angle of a member equipped with a sensor, detection power largely differs according to an operating direction of the member equipped with a sensor. In such a case, the member and the subject are repeatedly forced into contact with each other and plural signals from the sensor can improve detection accuracy.

In the present invention, when dust adheres to or is put on a subject, since the plate is contacted and pressed against the subject as shown in FIG. 3, a contact portion of the plate strips or removes the dust. Accordingly, since the contact portion thereof does not vibrate due to dust, the dust is not mistaken for a convexity.

In contrast, according to a conventional optical method of using a laser beam or a method disclosed in Japanese Laid-Open Patent Publication No. 2000-214100 of contacting a roll to a subject, most dust particles on a surface of a subject are mistaken for convexities and an additional process of dust removal such as blowing air is indispensable before convexity detection can be achieved.

In the present invention, as mentioned above, such a dust removal process of a conventional method is not necessary. Therefore, the detection method of the present invention is simpler, one of advantages of the present invention. However, detection accuracy becomes higher if a dust particle is removed before detection even in the detection method of the present invention.

Figure 4:
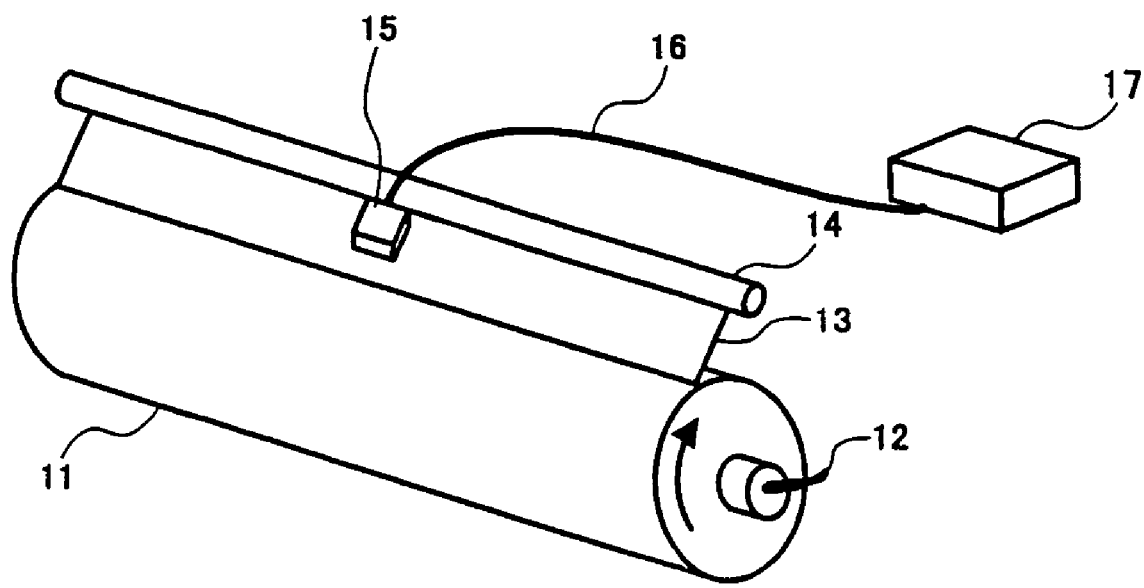
FIG. 4 is a schematic view illustrating a third embodiment of the detector of the present invention.

FIG. 4 is a schematic view illustrating a third embodiment of the detector of the present invention, having a sensor 15 on its plate 13. In FIG. 4, numeral 11 is a roller, or a belt supported with a roll inside, and numeral 12 is an axis therefor and rotatable in a direction indicated by an arrow. Numeral 13 is a plate, 14 is a hinge holding the plate, forcing the plate to contact a subject and releasing the plate therefrom, 15 is a vibration or pressure sensor, 16 is a cable transmitting a signal from the sensor, and 17 is a processor processing the signal.

Figure 5:
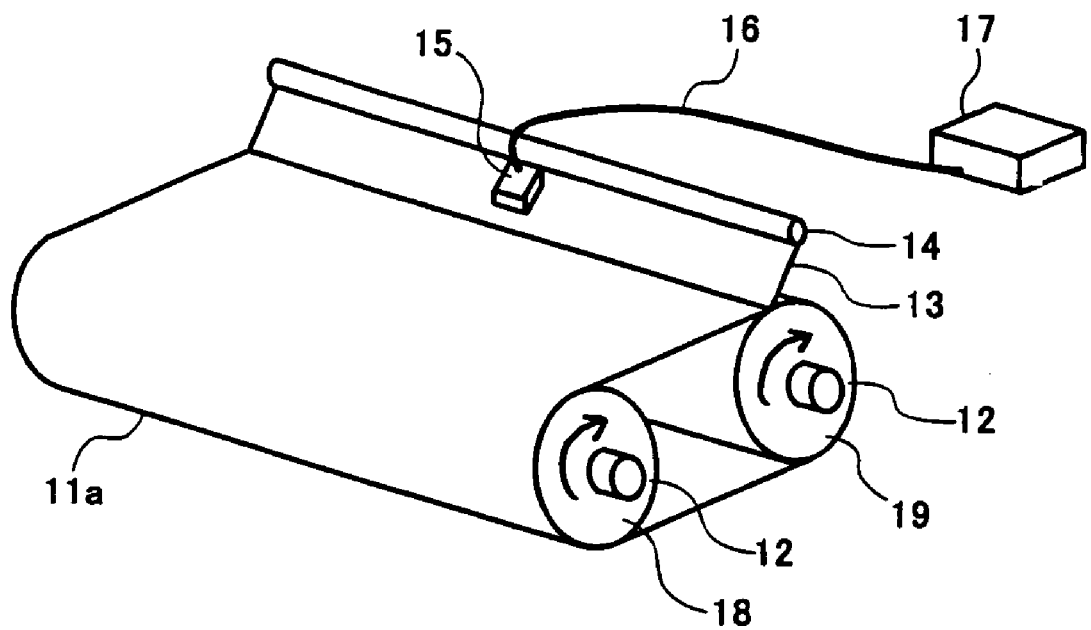
FIG. 5 is a schematic view illustrating a fourth embodiment of the detector of the present invention.

FIG. 5 is a schematic view illustrating a fourth embodiment of the detector of the present invention, having a sensor 15 on its plate 13, and two rolls 18, 19 supporting a belt 11a from within, the belt 11a being hanged between the rolls 18, 19. In FIG. 5, numeral 11a is belt, 18 and 19 are rolls hanging the belt, 12 are their axes, 13 is a plate, 14 is a hinge holding the plate, forcing the plate to contact a subject and releasing the plate from the subject, 15 is a vibration or pressure sensor, 16 is a cable transmitting a signal from the sensor, and 17 is a processor processing the signal.

Figure 6:
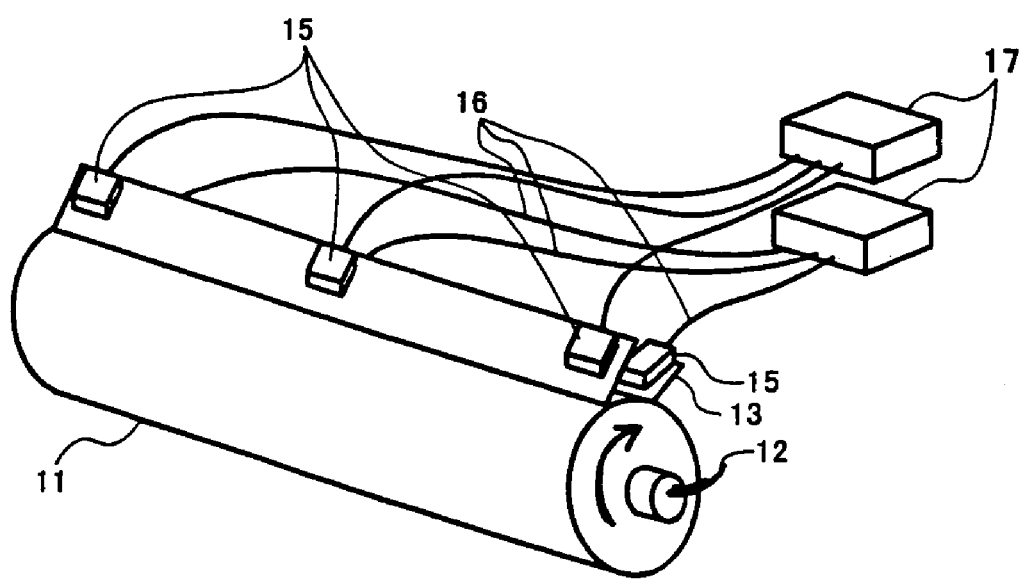
FIG. 6 is a schematic view illustrating a fifth embodiment of the detector of the present invention.

FIG. 6 is a schematic view illustrating a fifth embodiment of the detector of the present invention, having two plates 13a, 13b with three sensors 15 each, and two processors 17. In FIG. 6, numeral 11 is a roller, or a belt supported with an inner roll, and numeral 12 is an axis therefor and rotatable in a direction indicated by an arrow. Numeral 13 is a plate, 15 is a vibration or pressure sensor, 16 is a cable transmitting a signal from the sensor, and 17 are processors processing the signal.

After a convexity is detected by a sensor, the convexity is detected by another sensor again. Therefore, even when there is a wide variety of convexities in terms of number, forms, and sizes, and when a single sensor and detector circuit cannot detect them, plural sensors, mounting members and detector circuits (hereinafter referred to as a sensor unit) can be provided. The sensor units are respectively optimized according to the convexities, and can detect them better than a single sensor.

For example, when there are both convexities of large waviness having a height of a few mm, as well a micro-protrusion convexities having a height of a few µm, both a sensor unit to detect the large waviness and a sensor unit to detect the micro-protrusion can detect the two convexities.

Figure 7A:
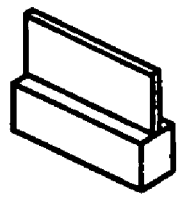
FIGS. 7A through 7E (collectively referred to as "FIG. 7") are schematic views illustrating embodiments of the plate contact member (also called a "contact plate" or simply "plate") of the detector of the present invention.
Figure 7B:
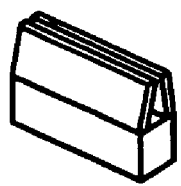
Figure 7C:
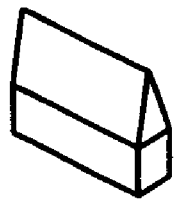
Figure 7D:
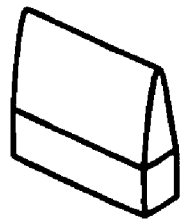
Figure 7E:
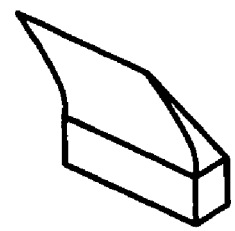

FIGS. 7A through 7E (which may collectively be referred to as "FIG. 7") are schematic views illustrating embodiments of the plate of the detector of the present invention, with their contact portions turned up for purposes of illustration. Plate edges are preferably sharp to detect a convexity. FIG. 7a is a standard type plate, FIG. 7b is a type having two plates, FIG. 7c is a three-corner plate, FIG. 7d is a plate having a curved-surface edge, and FIG. 7e is an inclined plate.

Figure 8:
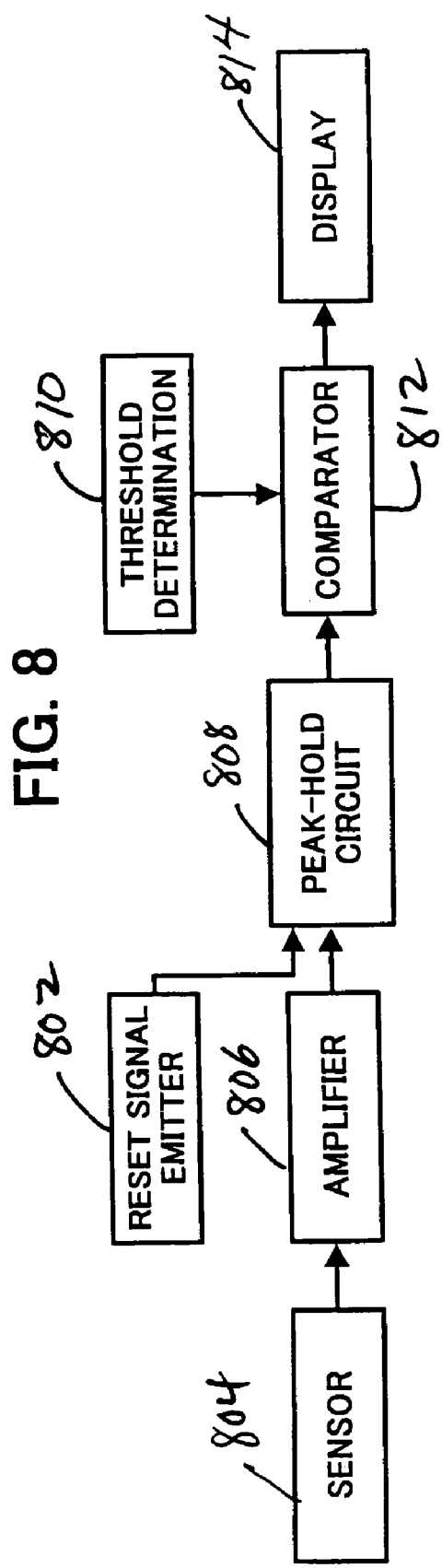
FIG. 8 is a block diagram showing a peak hold mechanism.

FIG. 8 is an exemplary block diagram of the signal processing mechanism of the detector shown in FIG. 4 or 5. A signal from a reset signal emitter 802 enters a peak hold circuit 808 just before detection, and the peak hold circuit 808 is reset.

After the reset process, a signal from a sensor 804 is amplified with an amplifying circuit 806 and enters the peak hold circuit 808. The peak hold circuit 808 is a circuit recording a strength of the largest signal input to it at a time, and the maximum strength recorded at a time is output at any time or when a request signal (not shown) is input. Then, the maximum strength is compared by a comparator 812 with a threshold input from a threshold determination portion 810. More specifically, the maximum strength may be compared with a standard (acceptable tolerance), and the result is displayed on display 814. All or part of the process can be implemented in software.

Also according to the present invention, a signal of a vibration or a change of pressure detected by a sensor is passed through a frequency filter to remove unnecessary frequency members, and a protrusion or a surface variation can more accurately be detected.

Figure 9:
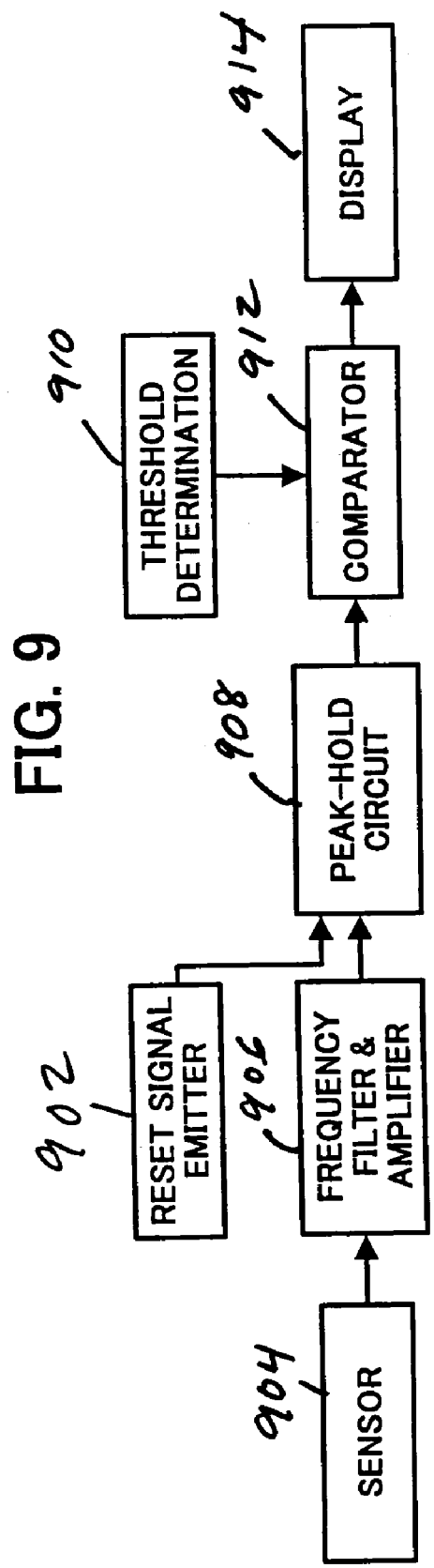
FIG. 9 is a block diagram showing a peak hold mechanism equipped with a frequency filter.

FIG. 9 is a block diagram showing how a signal from a sensor 904 enters a peak hold circuit 908 after passed through a frequency filter and amplifying circuit 906. A signal from a reset signal emitter 902 enters peak hold circuit 908 just before detection, and the peak hold circuit is reset. The computed peak value is compared by comparator 912 with a threshold input from threshold determination portion 910; more specifically, the computed peak value is compared with a standard (acceptable tolerance), and the result is displayed on a display 914. All or part of the process can be implemented in software.

FIG. 10 is a block diagram showing computing of a frequency distribution of a signal from a sensor 1004, and the frequency distribution of the signal from the sensor is computed with an instruction from a trigger circuit 1002 after passed through an amplifying circuit 1006. In FIG. 10, a FFT processor 1008 computes the frequency distribution with a mechanism such as a Fourier transform. The frequency distribution computed by the FFT processor 1008 is compared by comparator 1012 with a threshold input from threshold determination portion 1010. More specifically, the frequency distribution is compared with a standard (acceptable tolerance), and the result is displayed on a display 1014.

FIG. 11 is a block diagram showing processing of a signal from a sensor 1104 with a short-time Fourier transform. In FIG. 11, a STFT processor 1108 has a mechanism performing the short-time Fourier transform. The mechanism computes a time-frequency analysis or a spectrogram of a vibration or a change of pressure with the short-time Fourier transform. The short-time Fourier transform may be a short-time high speed Fourier transform using a speedup algorithm. A part of the process can be implemented in software. Threshold determination portion 1110, comparator 1112, and display 1114 perform functions analogous to those described with reference to previously-described embodiments, and accordingly discussion thereof is omitted.

FIG. 12 is a block diagram showing processing of a signal from a sensor 1204 with a wavelet transform. In FIG. 12, a processor 1208 has a mechanism performing the wavelet transform. The mechanism performs a multiple resolution analysis of a vibration or a change of pressure with the wavelet transform. A part of the process can be implemented in software. Trigger circuit 1202, amplifier 1206, threshold determination portion 1210, comparator 1212, and display 1214 perform functions analogous to those described with reference to previously-described embodiments, and accordingly discussion thereof is omitted.

FIG. 13 is a block diagram showing processing of a signal from a sensor 1304 with a bandpass filter. In FIG. 13, a processor 1308 has a mechanism performing the bandpass filter process. The mechanism performs a multiple resolution analysis of a vibration or a change of pressure with the bandpass filter process. A part of the process can be implemented in software. Trigger circuit 1302, amplifier 1306, threshold determination portion 1310, comparator 1312, and display 1314 perform functions analogous to those described with reference to previously-described embodiments, and accordingly discussion thereof is omitted.

Figure 14:
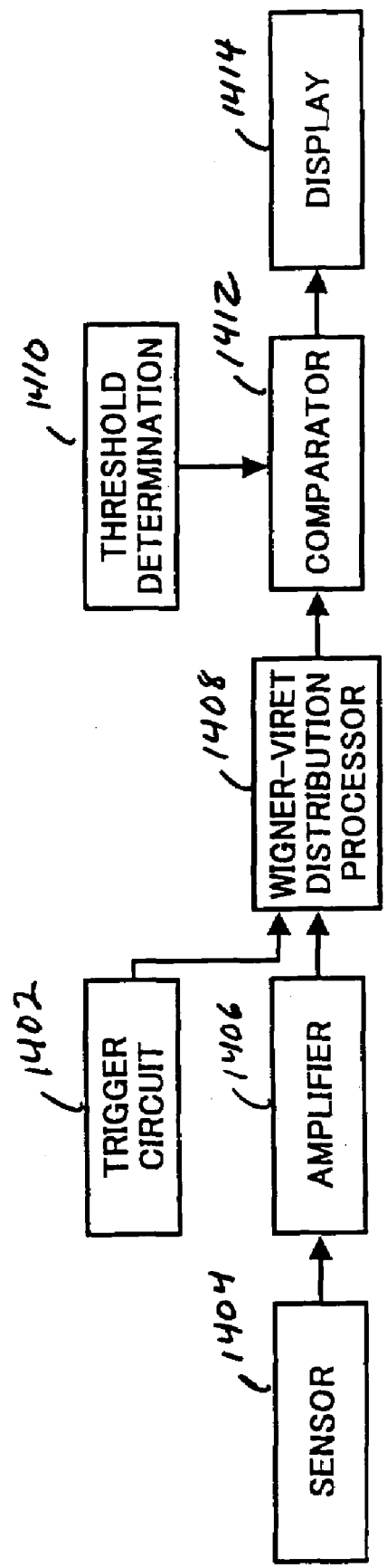
FIG. 14 is a block diagram showing a mechanism performing a Wigner distribution.

FIG. 14 is a block diagram processing of a signal from a sensor 1404 with a Wigner distribution. In FIG. 14, a processor 1408 has a mechanism computing the Wigner distribution. The mechanism performs a multiple resolution analysis of a vibration or a change of pressure with the Wigner-Viret distribution. A part of the process can be implemented in software. Trigger circuit 1402, amplifier 1406, threshold determination portion 1410, comparator 1412, and display 1414 perform functions analogous to those described with reference to previously-described embodiments, and accordingly discussion thereof is omitted.

The display shown in FIGS. 8 to 14 displays the result of an evaluation of a convexity. The display may be implemented as a lamp, LED, CRT or liquid crystal display. Instead of being displayed, the convexity evaluation can be electrically or optically transmitted to other devices.

The display can show a detected convexity, its location and size, a result of comparing the convexity with a threshold, and other items that may be detected and processed with the methods of the present invention. In addition, the display may be combined with the detection apparatus of the present invention and arranged close to or remote from a production line of the belt or the roller to from a production system.

Figure 15:
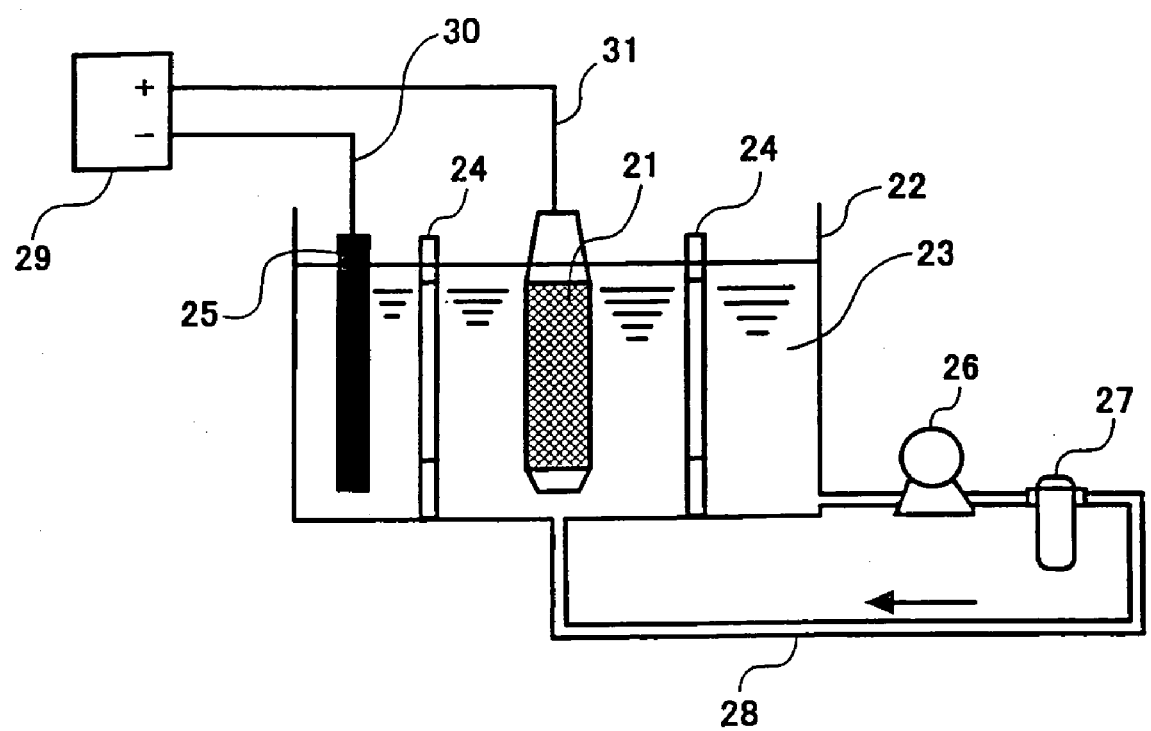
FIG. 15 is a schematic view illustrating an embodiment of the electroforming apparatus of the present invention.

FIG. 15 is a schematic view illustrating an embodiment of an electroforming apparatus to prepare a nickel belt that may be one of the belts used according to the present invention.

In the electroforming apparatus shown in FIG. 15, a metal mold 21 as a cathode is dipped in an electroforming tank 22 containing a sulfamic acid liquid as an electroforming liquid 23, and framed with a cathode case 24 equipped with a cathode slit preventing an anion that is a cause of a gas formation from passing through the case.

A nickel anode 25 is arranged in the electroforming tank 22 as a counterpart of the cathode, i.e., the metal mold 21, and direct-current electricity from a rectifier 29 is applied to the anode 25 and the cathode of metal mold 21 through wires 30 and 31.

The metal mold 21 is arranged so as to be rotated with a rotator (not shown), and a pipe 28 circulates the electroforming liquid 23 in the electroforming tank 22. Pipe 28 has a barrier filter 27 for the electroforming liquid 23, to revitalize the liquid. A circulation pump 26 pumps the unfiltered liquid from the tank 22 and feeds the revitalized liquid to the tank.

The detection method of the present invention, as mentioned above, can detect any convexities on surfaces of various members for use in an electrophotographic image forming apparatus. In particular, a ground swell and an arcuation like a moderate arc, or a micro-protrusion, can be detected, and the detection method of the present invention can further be used for recycled members.

In addition, the detection method of the present invention using a plate alone, or a plate with a sensor, can inspect not only a peripheral surface of a subject but also an inside surface of a belt, e.g., an inside surface of a metallic belt that is coated by a spray coating method.

Further, when a member having a convexity detected by the detection method of the present invention does not conform to a standard (tolerance range) for the member of an electrophotographic image forming apparatus, the defective member thus detected may be removed from a manufacturing process. Therefore, when the detection apparatus of the present invention is installed in a production lines of members (such as belts or rollers), a production system having a high efficiency can be constructed. In this case, the apparatus can be equipped with the display described above.

Having generally described this invention, further understanding can be obtained by reference to certain specific examples that are provided herein for the purpose of illustration only, and that are not intended to limit the scope of the invention.

EXAMPLES

First, a method of producing a nickel belt, which is one belt to be inspected, will be explained.

Preparation for an Electroforming Liquid

Five to 30 g/L of halogenated nickel (nickel chloride or nickel bromide), 20 to 40 g/L of boric acid, an adequate dose of Nickelight S from Nihon Kagaku Sangyo Co., Ltd. and 1 to 20 g/L of 2-ethyl sodium sulfate were additively included in 350 to 600 g/L of a nickel sulfamate liquid from Nihon Kagaku Sangyo Co., Ltd. to prepare 400 L of an electroforming liquid.

Electroforming Conditions

In the apparatus shown in FIG. 15, a stainless metal mold was used for the cathode, and a Nickel S Pellet from Shimura Kako Co., Ltd. was used for the anode. A current-carrying time was 125A×30 min, a number of revolutions of the metal mold was 6 rpm and a temperature of the electroforming liquid was 50° C.

In addition, a metal mold was formed of a steel tube for piping from SUS304. The metal mold has a 1 mm smaller diameter at the upper end thereof, having a length about 25 mm; this portion is used as a upper end cut portion of a precipitated nickel film. The metal mold has a 1 mm smaller diameter at the lower end thereof, having a length about 25 mm; this portion is used as a lower end cut portion of the precipitated nickel film. A portion between the upper and lower ends is a precipitated portion for a nickel belt; the surface roughness (R max) is 0.5.

On these electroforming conditions, fifty seamless nickel belts having a diameter of 168 mm, a width of 466 mm and a thickness of 30 μm were prepared. Next, both ends of each nickel belt were cut such that the belt had a width of 420 mm. Ten nickel belts respectively having different degrees of protrusion were selected from these 50 nickel belts. The thus prepared belts were numbered from 1 to 10.

Example 1

This example involves detecting a convexity by detecting sound arising when the plate and belt contact each other.

Each of the thus prepared nickel belts was set in the apparatuses shown in FIGS. 1 and 2.

In FIG. 2, the roll having the nickel belt on was rotated while the plate 13 contacted the nickel belt, and a sound emitted from the plate 13 was sensed. A polyester film having a thickness of 100 μm, a width of 40 mm and a length of 420 mm, which was prepared by a biaxial stretching method was used as the plate.

In addition, a contact angle of the plate was 45°, i.e., the angle B shown in FIG. 3 was 45°. The roll having the nickel belt on was rotated at a speed of from 25 to 35 rpm.

This operation was performed repeatedly on each of the ten nickel belts, and the results are shown in Table 2.

Belts 1 and 4 emitted a sound, and belt 7 emitted two sounds.

An optical microscope found that belt 1 had a convexity having a height of about 35 μm and a diameter of about 50 μm, and that belt 4 had a convexity having a height of about 45 μm and a diameter of about 60 μm.

In addition, the microscope found that belt 7 had a convexity having a height of about 35 μm and a diameter of about 40 μm and a convexity having a height of about 25 μm and a diameter of about 50 μm at an interval of about 12 mm therebetween.

The other belts emitted only normal friction sounds, and did not emit any sound that might be due to a convexity.

As a result, it was determined that belts 1 and 4 each had a convexity, belts 7 had two convexities, and the other belts did not have a convexity.

Example 2

This example involves detecting a convexity by a peak hold process on a signal detected by a plate with a sensor.

Each of the above-mentioned ten nickel belts was set in the apparatus shown in FIG. 5, and the roll having the nickel belt on was rotated while the plate 13 contacted the nickel belt and vibration generated on the plate 13 was detected by a vibration sensor using a piezoelectric device.

The signal processing shown in FIG. 9 was used. A polyester film having a thickness of 100 μm, a width of 40 mm and a length of 420 mm, that was prepared by a biaxial stretching method, was used as the plate.

In addition, a contact angle of the plate was 45°, i.e., the angle B shown in FIG. 3 was 45°. The thus evaluated results are shown in Table 2.

One convexity detection was performed on belts 1, 4 and 9, and two convexity detections were performed on belt 7.

A signal of the convexity detected from belt 9 was smaller than those of belts 1 and 4. An optical microscope found that the convexity of belt 9 had a height of 25 μm and a diameter of 30 μm, and was smaller than those of belts 1 and 4.

In addition, the convexity detected from each of belts 1, 4 and 7 was the same convexity detected in Example 1.

As a result, it was determined that belts 1, 4 and 9 each had one convexity, belt 7 had two convexities, and the other belts had no convexity.

Example 3

This example involves detecting a convexity by comparing a frequency distribution computed from a signal detected from a sensor-equipped plate with a threshold.

Each of the above-mentioned ten nickel belts was set in the apparatus shown in FIG. 5, and the roll having the nickel belt on was rotated while the plate 13 contacted the nickel belt and vibration generated on the plate 13 was detected by a vibration sensor using a piezoelectric device.

A polyester film having a thickness of 100 μm, a width of 40 mm and a length of 420 mm, that was prepared by a biaxial stretching method, was used as the plate 13.

In addition, a contact angle of the plate was 30°, i.e., the angle B shown in FIG. 3 was 30°.

The signal processing shown in FIG. 10 was used, and a Fourier transform was performed to determine frequency distribution. The thus evaluated results are shown in Table 2.

One convexity detection was performed on belts 1, 4 and 9, and two convexity detections were performed on belt 7.

A signal of the convexity detected from belt 9 was smaller than those of belts 1 and 4.

In addition, the convexity detected from belts 1, 4, 7 and 9 was the same convexity detected in Example 2.

As a result, it was determined that belts 1, 4 and 9 each had one convexity, belt 7 had two convexities, and the other belts had no convexity.

Example 4

This example involves detecting a convexity using a short-time Fourier transform as a multiple resolution analysis.

Each of the above-mentioned ten nickel belts was set in the apparatus shown in FIG. 4, and the roll having the nickel belt on was rotated while the plate 13 contacted the nickel belt and vibration generated on the plate 13 was detected by a vibration sensor using a piezoelectric device.

The signal processing shown in FIG. 11 was used, and the short-time high speed Fourier transform was performed. The short-time high speed Fourier transform is a combined method of a Fourier transform and a high-speed Fourier transform, and performs a same result as that of a normal short-time Fourier transform.

A polyester film having a thickness of 100 μm, a width of 40 mm and a length of 420 mm, that was prepared by a biaxial stretching method, was used as the plate 13.

In addition, a contact angle of the plate was 45°, i.e., the angle B shown in FIG. 3 was 45°.

The thus evaluated results are shown in Table 2.

One convexity detection was performed on belts 1, 4 and 9, and two convexity detections were performed on belt 7.

A signal of the convexity detected from belt 9 was smaller than those of belts 1 and 4.

In addition, the convexity detected from each belt 1, 4, 7 and 9 was the same convexity detected in Example 2.

As a result, it was determined that belts 1, 4 and 9 each had one convexity, belt 7 had two convexities, and the other belts had no convexity.

Example 5

This example involves detecting a convexity using a wavelet transform as a multiple resolution analysis.

Each of the above-mentioned ten nickel belts was set in the apparatus shown in FIG. 4, and the roll having the nickel belt on was rotated while the plate 13 contacted the nickel belt and vibration generated on the plate 13 was detected by an electret condenser microphone from Sony Corp.

The signal processing shown in FIG. 12 was used, and the wavelet transform was performed. The 8th Daubechies function was used as a wavelet function for the wavelet transform.

A polyester film having a thickness of 100 μm, a width of 40 mm and a length of 420 mm, that was prepared by a biaxial stretching method, was used as the plate 13.

In addition, a contact angle of the plate was 30°, i.e., the angle B shown in FIG. 3 was 30°.

The inspection results of the ten belts are shown in Table 2.

One convexity detection was performed on belts 1, 3, 4 and 9, and two convexity detections were performed on belt 7.

Signals of the convexity detected from belts 3 and 9 were smaller than those of belts 1 and 4.

An optical microscope found that the convexity of belt 3 had a moderate form, having a height of 40 μm and a diameter of 150 μm.

In addition, the convexity detected from each belt 1, 4, 7 and 9 was the same convexity detected in Example 2.

As a result, it was determined that belts 1, 3, 4 and 9 each had one convexity, belt 7 had two convexities, and the other belts had no convexity.

In this example, a convexity having a moderate form was found on belt 3 for the first time. This is because the wavelet transform was capable of detecting a signal from the moderate convexity of belt 3.

Further, the procedures of evaluation of the nickel belts in Examples 1 to 5 were repeated, except that the contact angle of the plate contact member was changed from 30° to 45° and 80° to find that belts 1, 3, 4, 7 and 9 had a convexity and that the detection capability did not largely change when the contact angle of the plate contact member was from 30° to 80°.

Figure 16:
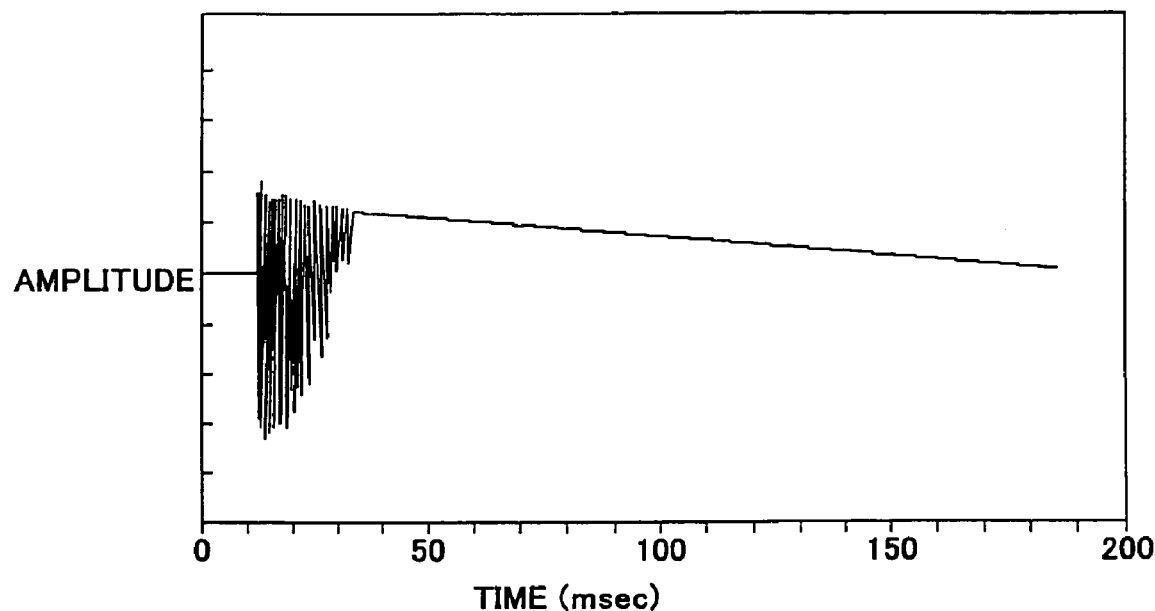
FIG. 16 is a chart of an original signal detecting a protrusion of a nickel belt.

In the examples of the present invention, an example of a signal detected by the microphone when the belt was inspected is shown in FIG. 16. A result of a wavelet transform on the signal is shown in FIG. 17.

Figure 17:
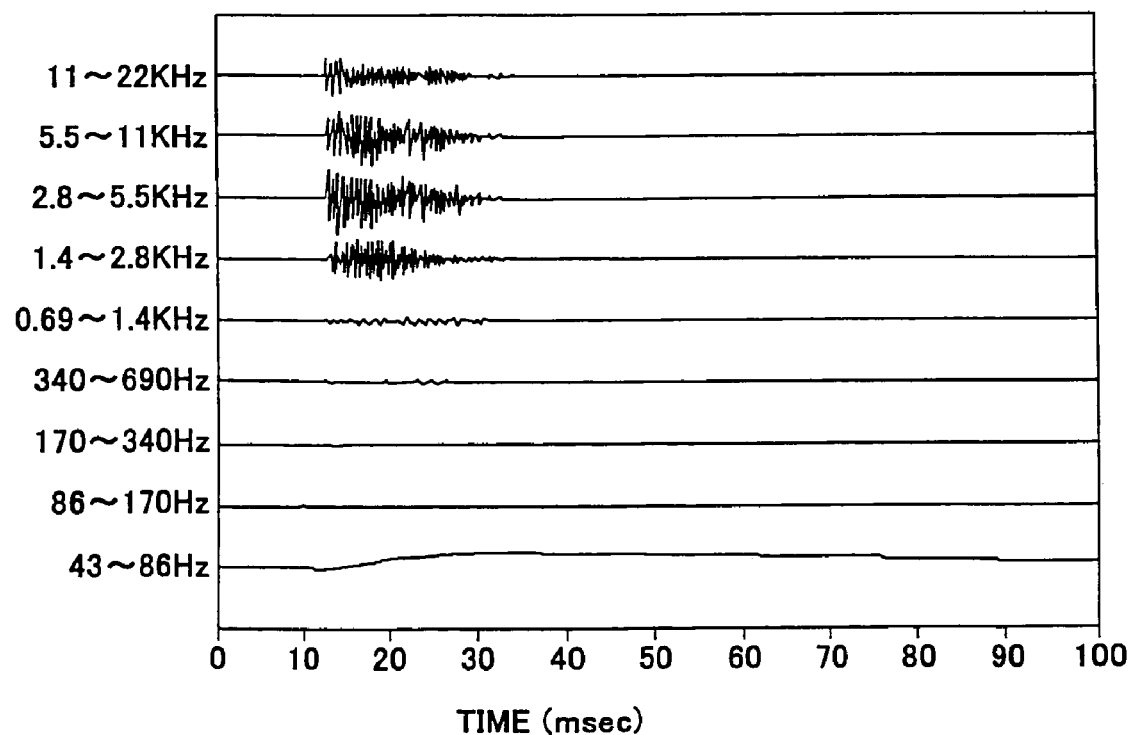
FIG. 17 is a chart showing a wavelet transform result of a protrusion signal of a nickel belt.

In order to see a variation status of a signal before a convexity is detected, a signal variation about 12 msec before a convexity is detected is shown In FIGS. 16 and 17.

An original detected signal shown in FIG. 16 has a large amplitude after a convexity is detected and a base line largely declines later. A result of a multiple resolution analysis performed on the signal is shown in FIG. 17, in which the original signal is divided into 9 frequency bands and temporal responses thereof are shown.

In FIG. 17, presence of vibrations are identified in four frequencies, i.e., of from 11 to 22 KHz, from 5.5 to 11 KHz, from 2.8 to 5.5 KHz and from 1.4 to 2.8 KHz. In addition, a presence of vibration is also identified in a low frequency of from 43 to 86 Hz. However, a presence of a strong vibration is not identified between 86 Hz and 1400 Hz. In this manner, a tendency of a frequency distribution can be known without losing time information of a signal obtained from a sensor by the multiple resolution analysis.

Therefore, in detection and evaluation of a convexity, when a controversial frequency range is revealed before detection and the multiple resolution analysis is performed on a signal of a vibration from a sensor to evaluate the controversial frequency, the evaluation can accurately be performed.

For example, it is difficult to make a decision to pass or fail only from the result shown in FIG. 16. However, when the multiple resolution analysis is performed on this to obtain the result shown in FIG. 17 and it is determined based only on a frequency range not less than 1.4 KHz, a more precise decision can be made because affects of the low frequencies in FIG. 16 are removed.

A moderate ground swell can be accurately detected when a pressure variation sensor is used and the multiple resolution analysis is performed on a signal therefrom as shown in FIG. 17 to make a decision based on a change of signal in a low frequency range.

Example 6

This example involves detecting a convexity by performing a bandpass filter process as a multiple resolution analysis.

Each of the above-mentioned ten nickel belts was set in the apparatus shown in FIG. 3 so as to be supported from inside by a roll. The roll having the nickel belt on was rotated while the plate 13 contacted the nickel belt and vibration generated on the plate 13 was detected by an electret condenser microphone from Sony Corp.

The signal processing shown in FIG. 13 was used, and multiple resolution analysis with a bandpass filter was performed.

A polyester film having a thickness of 100 μm, a width of 40 mm and a length of 420 mm, that was prepared by a biaxial stretching method, was used as the plate 13.

In addition, a contact angle of the plate was 45°, i.e., the angle B shown in FIG. 3 was 45°.

The thus evaluated results are shown in Table 2.

One convexity detection was performed on belts 1, 3, 4 and 9, and two convexity detections were performed on belt 7. The convexity detected from each belt 1, 4, 7 and 9 was the same convexity detected in Example 5.

Example 7

This example involves detecting a convexity using a Wigner distribution as a multiple resolution analysis.

Each of the above-mentioned ten nickel belts was set in the apparatus shown in FIG. 3, and the roll having the nickel belt on was rotated while the plate 13 contacted the nickel belt and vibration generated on the plate 13 was detected by an electret condenser microphone from Sony Corp.

The signal processing shown in FIG. 14 was used, and the Wigner distribution was determined.

A polyester film having a thickness of 100 μm, a width of 40 mm and a length of 420 mm, that was prepared by a biaxial stretching method, was used as the plate 13.

In addition, a contact angle of the plate was 45°, i.e., the angle B shown in FIG. 3 was 45°.

The thus evaluated results are shown in Table 2.

One convexity detection was performed on belts 1, 3, 4 and 9, and two convexity detections were performed on belt 7.

Results of the Wigner distribution of belts 3 and 9 was lower than those of belts 1 and 4, and the convexities of belts 3 and 9 were supposed to smaller than those of belts 1 and 4.

The convexity detected from each of belts 1, 4, 7 and 9 was the same convexity detected in Example 5.

Comparative Example 1

This example involves detecting a convexity by touching with a hand, as conventionally used.

A nickel belt was set in the apparatus shown in FIG. 1, and the hinge 4 was rotated such that the plate 13 did not contact the belt. Next, a polyethylene globe was put on a hand, and further a polyester fiber glove for a clean room was put thereon to check whether there was a protrusion on a surface of the belt while roll 1 was rotated. The thus evaluated results are shown in Table 2.

A convexity on each of belts 4 and 7 was detected. However, the convexity of belt 1 commonly detected in Examples 1 to 7, and the convexity detected on belts 3 and 9, could not be detected.

It was found that the polyethylene glove and the polyester fiber glove put on a hand were not suitable for detecting a microscopic convexity.

In this method, it can be considered that only the polyester fiber glove is used, but oil from the hand occasionally adheres to a surface of a subject, actually causing a defect of the subject.

In addition, only the polyethylene glove is not suitable for detecting a microscopic convexity because of its roughness. It can be considered that a thin rubber glove is used, but a coefficient of friction between the rubber glove and a subject is so large that it is difficult to abrade a surface of the subject by hand with a rubber glove.

Comparative Example 2

This example involves detecting a convexity by a conventional method using a laser beam.

A nickel belt was set in the apparatus shown in FIG. 1, and the hinge 4 was rotated such that the plate 13 did not contact the belt. Next, a laser beam irradiated the belt to check the scattered light. The laser beam had a wavelength of 780 μm and a spot diameter of 60 μm. The thus evaluated results are shown in Table 2.

A convexity on each of belts 1, 4 and 8 was detected. Two convexities on belt 7 were detected. The convexity detected on belt 1 was the same convexity detected in Examples 1 to 7.

However, the convexity detected on belt 4 had a different location from that of the convexity detected in Examples 1 to 7.

The convexity was further investigated to find that it was an amorphous dust having a size of about 20 μm.

In addition, the convexity of belt 8 was not detected in Examples 1 to 7, and the convexity was further investigated to find that it was a fibriform material having a diameter of about 10 μm and a length of 70 μm.

Therefore, it was found that this method not only had insufficient detection capability, but also misidentified a dust particle adhering to a surface of a subject as a convexity.

Comparative Example 3

Using a Roll Instead of a Plate

This example involves detecting a convexity by contacting another roller to a surface of a subject, as disclosed in Japanese Laid-Open Patent Publication No. 2000-214100.

A nickel belt was set in an apparatus equipped with a roller having an outside diameter of 15 mm and a width of 420 mm. The thus evaluated results are shown in Table 2.

A convexity on each of belts 2, 7 and 8 was detected. The convexity detected on belt 1 was the same convexity detected in Examples 1 to 7.

However, two convexities were detected on belt 7 in Examples 1 to 7, but only one convexity was detected in this Comparative Example. This is because the two convexities were close to each other, and the roller identified them as a single convexity.

In addition, a convexity was not detected on belt 8 in Examples 1 to 8, but it was detected in this comparative example. The convexity was further investigated to find that it was a fibriform material having a diameter of about 10 μm and a length of 70 μm.

Therefore, it was found that this method not only had insufficient detection capability, but also misidentified a dust particle adhering to a surface of a subject as a convexity.

Preparation for Photoreceptors

Next, an electrophotographic photoreceptor having a substrate formed from each of the above-mentioned ten nickel belts was prepared by the following method.

1. Formation of an Undercoat Layer

A resin coating material (liquid) including the following components was coated on the nickel belt by a dip coating method, and the coated belt was heated at 150° C. for 15 min such that the coated material was hardened with the heat to form an undercoat layer having a thickness of 5 μm on a surface of the substrate.

| | |
|---|---|
| Titanium oxide | 20 parts by weight |
| Alkyd resin | 10 parts by weight |
| Melamine resin | 10 parts by weight |
| Methyl ethyl ketone | 60 parts by weight |

The alkyd resin was Bekkosol 1307-60-EL from Dainippon Ink & Chemicals, Inc. and the melamine resin was Super Bekkamin G-821-60 from Dainippon Ink & Chemicals, Inc.

2. Formation of a Charge Generation Layer

A resin coating material (liquid) including the following components was coated on the undercoat layer by the same dip coating method, and heated at 100° C. for 10 min to form a charge generation layer on the undercoat layer.

| | |
|---|---|
| Butyral resin | 1 part by weight |
| Disazo pigment | 9 parts by weight |
| Cyclohexane | 30 parts by weight |
| Tetrahydrofuran (THF) | 30 parts by weight |

Figure 18:
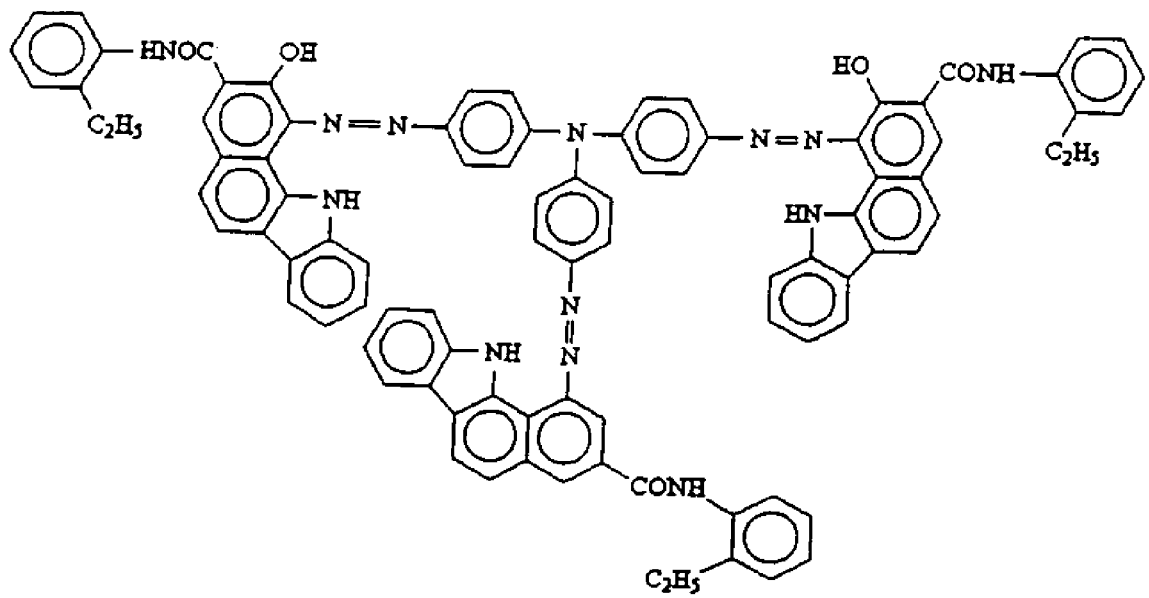
FIG. 18 shows the chemical structure of disazo pigment referenced in the description of the formation of a charge generation layer.

Disazo pigment has the formula shown in FIG. 18. The butyral resin was XYHL from Union Carbide Corp.

3. Formation of a Charge Transport Layer

Further, a resin coating material (liquid) including the following components was coated on the charge generation layer by the same dip coating method, and heated at 120° C. for 15 min to form a charge transport layer on the charge generation layer.

| | |
|---|---|
| Polycarbonate resin | 10 parts by weight |
| Charge transport material | 10 parts by weight |
| Dichloromethane | 80 parts by weight |

Figure 19:
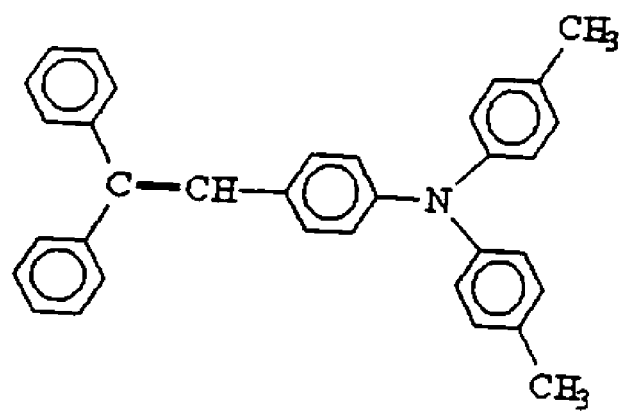
FIG. 19 shows the chemical structure of a charge transport material reference in the description of the formation of a charge transport layer.

The charge transport material has the formula shown in FIG. 19. The polycarbonate was Panlite K-1300 from Teijin Ltd.

Thus, an electrophotographic photoreceptor having a substrate formed from each of the above-mentioned ten nickel belts was prepared. The photoreceptors were sequentially numbered, e.g., the photoreceptor formed from belt 1 was numbered as a photoreceptor 1 and the photoreceptor formed from belt 2 was numbered as a photoreceptor 2.

Image Evaluation

The thus prepared ten electrophotographic photoreceptors were installed in a full-color laser printer from Ricoh Company, Ltd. and images were produced to evaluate quality of the images.

The laser printer has a laser beam wavelength of 780 nm, a beam diameter of 76 μm and an image resolution of 600 dpi. Half tone images were produced by the laser printer to check whether there was a defect in the images. The image evaluation results are shown in Table 1.

TABLE 1

| PHOTORECEPTOR NO. | IMAGE EVALUATION RESULTS |
|---|---|
| Photoreceptor 1 | Faint irregular color defect, the position of which conformed to a position of a protrusion on the nickel belt |
| Photoreceptor 2 | Good |
| Photoreceptor 3 | Good |
| Photoreceptor 4 | Irregular color defect, the position of which conformed to a position of a protrusion on the nickel belt |
| Photoreceptor 5 | Good |
| Photoreceptor 6 | Good |
| Photoreceptor 7 | Faint irregular color defect, the position of which conformed to a position of a protrusion on the nickel belt |
| Photoreceptor 8 | Good |
| Photoreceptor 9 | Faint irregular color defect, the position of which conformed to a position of a protrusion on the nickel belt |
| Photoreceptor 10 | Good |

TABLE 2

| EXAMPLE | EVALUATION RESULTS OF NICKEL BELT |
|---|---|
| Example 1 | Protrusion detected on belts 1, 4 and 7 |
| Example 2 | Protrusion detected on belts 1, 4, 7 and 9 |
| Example 3 | Protrusion detected on belts 1, 4, 7 and 9 |
| Example 4 | Protrusion detected on belts 1, 4, 7 and 9 |
| Example 5 | Protrusion detected on belts 1, 3, 4, 7 and 9 |
| Example 6 | Protrusion detected on belts 1, 3, 4, 7 and 9 |
| Example 7 | Protrusion detected on belts 1, 3, 4, 7 and 9 |
| Comparative Example 1 | Protrusion detected on belts 4 and 7 |
| Comparative Example 2 | Protrusion detected on belts 1, 4, 7 and 8 |
| Comparative Example 3 | Protrusion detected on belt 2, 7 and 8 |

In Example 1, a convexity could be detected on belts 1, 4 and 7. These convexities were relatively large protrusions having a diameter of from 30 to 50 μm and a height of from 30 to 50 μm.

In Examples 2 to 4, a convexity could be detected on belts 1, 4, 7 and 9. These convexities were very small protrusions having a diameter of about 5 μm and a height of about 8 μm.

In Examples 5 to 7, a convexity could be detected on belts 1, 3, 4, 7 and 9.

The convexity of belt 3 was a protrusion like a moderate ground swell having a diameter of about 50 μm and a height of about 5 μm.

In Comparative Example 1, a convexity on belts 4 and 7 could be detected, but a convexity on belts 1, 3 and 9 could not be detected.

In Comparative Example 2, a convexity was detected on belts 1, 4, 7 and 8, but a dust particle adhering to belt 8 was mistaken for a convexity. In addition, a small convexity of belt 9 could not be detected.

In Comparative Example 3, a convexity could be detected on belts 3 and 7, but a dust particle adhering to belts 2 and 8 was mistaken for a convexity. In addition, a convexity of belts 1, 3, 4 and 9 could not be detected.

Thus, an effect of the present invention could be recognized.

This document claims priority and contains subject matter related to Japanese Patent Applications Nos. 2001-284928, filed on Sep. 19, 2001; 2001-314849, filed on Oct. 12, 2001; and 2002-265198, filed on Sep. 11, 2002;

all of which are incorporated herein by reference.

Having now fully described embodiments of the invention, it will be apparent to one of ordinary skill in the art that many changes and modifications can be made thereto without departing from the spirit and scope of the invention as set forth herein.

What is claimed as new and desired to be secured by Letters Patent of the United States is:

1. A method of detecting a convexity present on a surface of a member, the method comprising:
    abrading a surface of the member with a plate;
    detecting the convexity by measuring at least one of a group including (1) vibration generated on the plate and (2) a change of pressure applied to the member;
    detecting at least one of the vibration and the change of pressure with a sensor provided on the plate;
    converting at least one of the vibration and the change of pressure into a digital signal;
    subjecting the digital signal to a multiple resolution analysis to determine a value; and
    comparing the value with a threshold;
    wherein the abrading step includes:
    first abrading the surface of the member by maintaining a direct engagement between the plate and the member while relatively moving the plate in a first direction, to measure at least one of a first vibration and a first change of pressure,
    thereafter secondly abrading the surface of the member while relatively moving the plate in a second direction opposite the first direction, to measure at least one of a second vibration and a second change of pressure; the plate configured such that the direct engagement results in the removal of dust in both the first and second directions; and
    repeating the first abrading and the second abrading steps to obtain plural signals from the sensor;
    wherein the detecting step includes analyzing the plural signals.

2. The method of claim 1, wherein:
    the member is belt-shaped; and
    the abrading step includes abrading the surface of the member with the plate while sandwiching the member with the plate and a rotating roller.

3. The method of claim 1, wherein:
    the member is roll-shaped; and
    the abrading step includes abrading the surface of the member with the plate while rotating the member.

4. The method of claim 1, wherein the abrading step includes:
    abrading the surface of the member with the plate at an angle of from 30° to 80°.

5. The method of claim 1, wherein the abrading step includes:
    abrading the surface of the member with the plate at a relative speed of from 5 to 100 mm/sec.

6. The method of claim 1, wherein the abrading step includes:
    abrading the surface of the member with the plate forming a contact portion, the abrading creating a pressure of from 0.00075 N to 0.0025 N when the contact portion has a width of 1 cm of an abrading portion thereof.

7. The method of claim 1, wherein the detecting step includes:
    detecting the vibration with a sound emitted from the plate and the member.

8. The method of claim 1, wherein the repeating step further includes the step of changing the speed of abrading.

9. The method of claim 1, further comprising:
    converting at least one of the vibration and the change of pressure into an electrical signal with the sensor;
    subjecting the electrical signal to a peak hold process to determine a maximum strength of the electrical signal; and
    comparing the maximum strength with a first threshold.

10. The method of claim 9, further comprising:
    processing the electrical signal to determine a frequency distribution thereof; and
    comparing the frequency distribution with a second threshold.

11. A method of selecting a subset of members having a predetermined tolerance from a plurality of members, the method comprising:
    detecting a convexity of each member of the plurality of members with the method of claim 1;
    determining whether the detected convexity is within a predetermined tolerance; and
    removing members having a detected convexity that is not within the predetermined tolerance.

12. The method of claim 1, wherein the subjecting step includes:
    subjecting the digital signal to the multiple resolution analysis with a method selected from a group consisting of short-time Fourier transforms, wavelet transforms, methods of determining a Wigner distribution and methods using a bandpass filter.

13. The method of claim 1, wherein:
    the member is belt-shaped and metallic and produced by an electroforming method.

14. The method of claim 1, wherein:
    a) plural sensors are provided at different positions of the plate, each sensor configured to provide a signal in response to detecting at least one of the vibration generated on the plate or the change of pressure applied to the member; and
    b) the detecting step includes:
        1) detecting at least one of a difference in detection time of said plural sensors and a difference in strength of the plural signals provided by the plural sensors; and
        2) processing the plural signals to determine at least one of a position and a size of the convexity.

* * * * *